United States Patent
Hathaway et al.

(10) Patent No.: US 10,398,305 B2
(45) Date of Patent: Sep. 3, 2019

(54) RETINAL THICKNESS

(71) Applicant: Cellview Imaging, Inc., Toronto (CA)

(72) Inventors: Mark Hathaway, Canterbury (GB); Rishard Weitz, Toronto (CA)

(73) Assignee: Cellview Imaging Inc. (CA)

( * ) Notice: Subject to any disclaimer, the term of this patent is extended or adjusted under 35 U.S.C. 154(b) by 54 days.

(21) Appl. No.: 15/318,267

(22) PCT Filed: Jun. 16, 2015

(86) PCT No.: PCT/CA2015/000382
§ 371 (c)(1),
(2) Date: Dec. 12, 2016

(87) PCT Pub. No.: WO2016/004508
PCT Pub. Date: Jan. 14, 2016

(65) Prior Publication Data
US 2017/0112374 A1     Apr. 27, 2017

Related U.S. Application Data
(60) Provisional application No. 62/022,332, filed on Jul. 9, 2014.

(51) Int. Cl.
*A61B 3/10* (2006.01)
*A61B 3/00* (2006.01)
*A61B 5/00* (2006.01)

(52) U.S. Cl.
CPC .......... *A61B 3/1005* (2013.01); *A61B 3/0008* (2013.01); *A61B 3/0025* (2013.01);
(Continued)

(58) Field of Classification Search
CPC ... A61B 3/1005; A61B 5/7257; A61B 5/7246; A61B 3/0025; A61B 3/0008;
(Continued)

(56) References Cited

U.S. PATENT DOCUMENTS
2012/0002164 A1   1/2012   Yamamoto et al.
2014/0218784 A1   8/2014   Wax et al.

FOREIGN PATENT DOCUMENTS
CA   2595324 A1   7/2006

OTHER PUBLICATIONS
Wojkowski M., et al, "In vivo human retinal imaging by Fourier domain optical coherence tomography," International Society for Optical Engineering, SPIE, vol. 7 No. 3, Jul. 1, 2002, pp. 457-463, XP002272406.
(Continued)

*Primary Examiner* — William R Alexander
*Assistant Examiner* — Henry A Duong
(74) *Attorney, Agent, or Firm* — Laubsher & Laubscher, P.C.

(57) ABSTRACT
A method is provided for determining the thickness of a retina. A single beam is used to illuminate the retina of a patient. Interference between reflections off different layers within the retina cause autocorrelation in the returned signal. An FFT applied to the autocorrelation signal reveals the strongest autocorrelation, which indicates the distance between the nerve fiber layer (NFL) and the layers between the inner segment/outer segment (IS/OS) and the retinal pigment epithelium (RPE), the dominant scatterers. By analyzing autocorrelation, a single beam can be used. This avoids the problem of movement of the patient, arising in the use of a standard OCT interferometer, resulting in a simpler and less expensive technique of measuring retinal thickness.

3 Claims, 2 Drawing Sheets

(52) U.S. Cl.
CPC ............ *A61B 3/102* (2013.01); *A61B 5/7246* (2013.01); *A61B 5/7257* (2013.01)

(58) Field of Classification Search
CPC ......... A61B 3/102; A61B 3/1225; A61B 3/12; A61B 3/103; A61B 3/1015; A61B 3/1233; A61B 3/1241
USPC ........................................................ 351/221
See application file for complete search history.

(56) References Cited

OTHER PUBLICATIONS

Mujat, Mircea, et al, "Retinal Nerve Fiber Layer Thickness Map Determined from Optical Coherence Tomography Images," Optics Express, Nov. 14, 2005, pp. 9480-9491, vol. 13 No. 23, Optical Society of America.

RETINAL THICKNESS

FIELD OF INVENTION

This invention relates to measurement of the thickness of a retina.

BACKGROUND

Retinal thickness in the central retina is frequently used to detect diseases in their early stages, and to monitor the effectiveness of treatment. Generally, images and data obtained with optical coherence tomography (OCT) systems are used. A standard spectral OCT system typically splits light from a single source into two parts, each of which traverses a different path in an interferometer. One path, called the reference path, simply introduces a variable delay into the beam travelling the reference path. The other path, called the object path, travels to and scatters back from a patient's eye. The light scattered back from the patient's eye is mixed with light from the reference path to produce an interference signal. The interference signal is analyzed with a spectrometer. For a usable OCT signal to be produced the two paths must be matched in length. However this means that patient movement tends to be an issue. Complicated image processing must be performed in order to compensate for patient movement when determining the retinal thickness when using a standard OCT system.

There is a need to provide a method of measuring retinal thickness using a simpler procedure, and which preferably does not depend on lack of movement by the patient.

SUMMARY

According to one embodiment of the invention, a method is provided for determining the thickness of a retina. The retina is illuminated with a beam of light. A beam reflected by the retina is received, and an autocorrelation signal within the reflected beam is used to determine the thickness of the retina.

According to another embodiment of the invention, a method of diagnosing retinal and/or ocular diseases in a patient is provided. A retina of the patient is illuminated with a beam of light. A beam reflected by the retina is received, and an autocorrelation signal within the reflected beam is used to determine the thickness of the retina. If the determined thickness of the retina is larger than a threshold, then it is concluded that retinal and/or ocular disease is present.

By using the autocorrelation signal of a reflected beam to determine the thickness of a patient's retina, movement by the patient need not be compensated for. Diagnosis of various retinal diseases is thereby simpler and more effective.

BRIEF DESCRIPTION OF THE DRAWINGS

The features and advantages of embodiments of the invention will become more apparent from the following detailed description of the preferred embodiment(s) with reference to the attached figures, wherein.

It is noted that in the attached figures, like features bear similar labels.

DETAILED DESCRIPTION OF THE PREFERRED EMBODIMENTS

The autocorrelation signal of a beam of light reflected by a patient's retina is produced by different reflections of the beam, reflecting off different layers of the retina, interfering with each other. The dominant scatterers in the retina are the nerve fiber layer (NFL) and the layers between the inner segment/outer segment (IS/OS) and the retinal pigment epithelium (RPE). Although mixing occurs between all layers, the dominant signal is produced by interference between light reflected off these two regions. Since reflections from each component are encoded in the same beam at the same time, movement by the patient is not an issue. This simplifies image processing.

Figure 1:
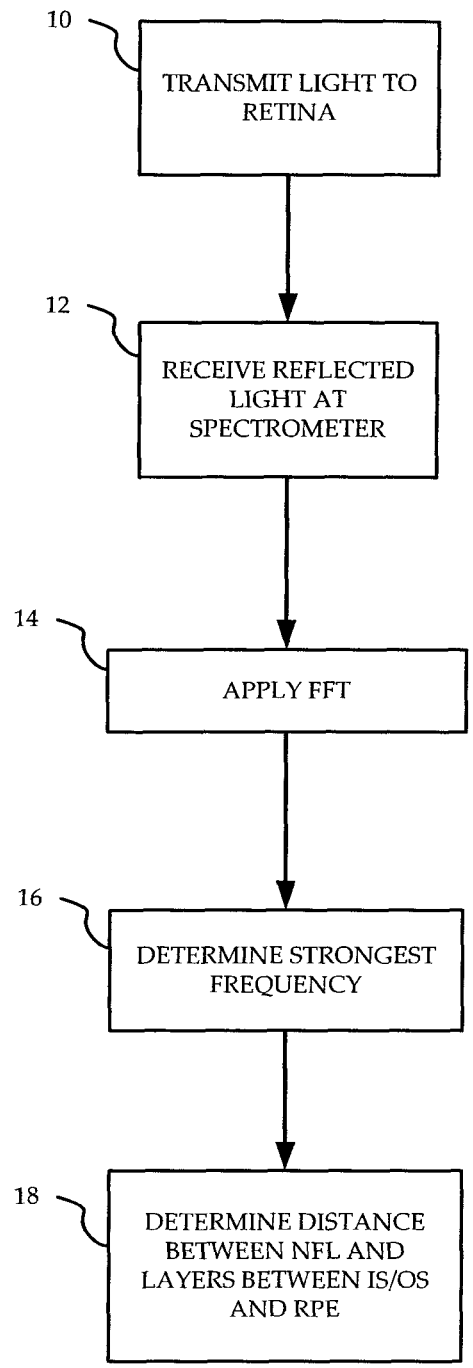
FIG. 1 shows a flowchart of a method by which the thickness of a retina is determined according to one embodiment of the invention.

Referring to FIG. 1, a flowchart of a method of determining the thickness of a retina according to one embodiment of the invention is shown. At step 10 a beam of light is transmitted towards a patient's retina. At step 12 a reflected beam from the patient's retina is received at a spectrometer. The step 12 of receiving a reflected beam from the patient's retina is carried out over an integration time.

At step 14 the spectrometer applies a fast Fourier transform to the beam received at step 12 and generates a frequency spectrum of the received beam. The frequency spectrum generated by the spectrometer contains multiple frequencies due to the distributed signals in the received beam, which in turn is due to distributed scattering by features throughout the depth of the retina. At step 16 a processor locates the strongest signal within the frequency spectrum. As explained above, the strongest frequency arises because of interferometry between the signal reflected from the NFL and the signal reflected from the layers between the IS/OS and the RPE. Once this frequency is determined, then at step 18 the distance between the NFL and the layers between the IS/OS and the RPE can be determined, and the thickness of the retina deduced.

Any of a number of different systems can be used to carry out the method described above with reference to FIG. 1. Because the interference is between different reflections within the same beam, an interference pattern does not require interference with a separate beam. In one embodiment, an optical coherence tomography (OCT) system is used to measure the thickness of a retina. In an OCT system, the autocorrelation signal is present in the scattered object beam reaching the interferometer. The autocorrelation signal is usually considered noise, and OCT systems are normally designed to suppress the autocorrelation signal relative to the OCT signal by suitable choice of reference beam power. This is possible because the OCT signal is a function of the reference beam power and the object beam power, whereas the autocorrelation signal is a function only of the object beam power. However according to this embodiment of the invention, measurement of the autocorrelation signal in the object beam is desired.

Figure 2:
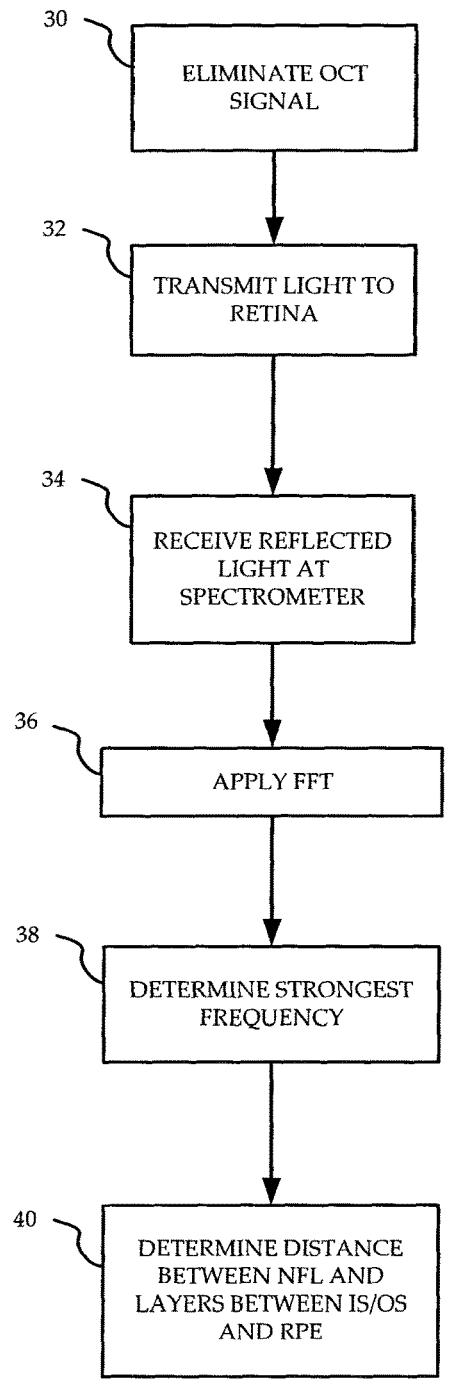
FIG. 2 shows a flowchart of a method by which the thickness of a retina is determined using an OCT system according to one embodiment of the invention.

Referring to FIG. 2, a flowchart of a method of determining the thickness of a retina using an OCT system according to one embodiment of the invention is shown. At step 30 the possibility of an OCT signal is eliminated, so that the only signal reaching the spectrometer of the OCT system will be the autocorrelation signal. The OCT signal is most easily eliminated by setting the reference path to an extreme position, such as at a maximum or a minimum length, resulting in no interference between the reference beam and the reflected beam within the object path. However other means of eliminating an OCT signal may be used, such as by attenuating the reference arm power.

At step 32 a beam of light is transmitted towards a patient's retina. At step 34 a reflected beam from the patient's retina is received at a spectrometer. Normally this beam would result from interference between a signal in the reference arm and a signal in the object arm, the latter being reflected from the patient's retina. However since the OCT signal has been eliminated at step 32, such as by extending the reference path to an extreme position, the only beam received by the spectrometer is the reflected beam within the object arm, and the autocorrelation signal is visible as more than just noise.

At step 36 the spectrometer applies a fast Fourier transform to the beam received at step 34 and generates a frequency spectrum of the received beam. The frequency spectrum generated by the spectrometer contains multiple frequencies due to the distributed signals in the received beam, which in turn is due to distributed scattering by features throughout the depth of the retina. At step 38 a processor locates the strongest signal within the frequency spectrum. As explained above, the strongest frequency arises because of interferometry between the signal reflected from the NFL and the signal reflected from the layers between the IS/OS and the RPE. Once this frequency is determined, then at step 40 the distance between the NFL and the layers between the IS/OS and the RPE can be determined, and the thickness of the retina deduced.

In another embodiment, a scanning laser ophthalmoscopy (SLO) system is used to measure the thickness of a retina. The avalanche photodiode (APD) or photomultiplier tube (PMT) normally found in an SLO system is replaced with a spectrometer in order to produce a frequency spectrum of the beam reflected from a patient's retina. Alternatively, the APD or PMT can be kept in place in order that the SLO functions can still be used, but part of the returned beam is split and sent to a spectrometer in order to produce a frequency spectrum of the reflected beam. Unlike an OCT system, there is no reference beam contributing to the beam received by the spectrometer and the spectrometer used in such an embodiment needs to be more sensitive than that used in an OCT system. However this greater sensitivity can be achieved with longer integration times and much less expensive charge-coupled devices (CCDs) or complementary metal-oxide-semiconductor (CMOS) arrays than are used in OCT systems. The step of receiving a reflected beam from the patient's retina is carried out over this longer integration time. A processor then determines the thickness of the retina from the frequency spectrum as described above.

In yet another embodiment, a fixed point measurement system is used to measure the thickness of a retina. The high sensitivity requirement of the spectrometer required for clear detection of the autocorrelation signal can be achieved with use of a 2D camera in the spectrometer, such as a low cost video CCD, in order to analyze light returned from the fixed point.

In the embodiments described above, the thickness of the retina is derived from an autocorrelation signal using a spectrometer. Alternatively, regular interferometry and variable path imbalance can be used to measure the thickness of the retina directly. As yet another alternative, a tunable laser and the Fourier domain can be used.

The methods described above for determining the thickness of a retina can be used in methods for screening and diagnosing of various retina and ocular diseases. Such disease include diabetic retinopathy, diabetic macular edema, age-related macular degeneration (AMD), cystoid macular edema, central serous retinopathy, central retinal vein occlusion, central retinal artery occlusion, and glaucoma. Retinal thickness increases dramatically in such diseases due to death of cells of specific inner or outer layers of the retina due to the above diseases at more progressive stages. Accordingly, in one embodiment of the invention the methods described above for determining the thickness of a retina are preliminary steps in a method for screening and/or diagnosing such diseases.

The logic of the methods described above may be stored as instructions stored on a non-transitory computer-readable storage medium in a form executable by a computer processor, although in the embodiment in which an OCT system is used to carry out the method the elimination the OCT signal may be carried out manually instead. The processor may be implemented by a general purpose processor, a network processor, a digital signal processor, an ASIC, or multiple such devices.

The embodiments presented are exemplary only and persons skilled in the art would appreciate that variations to the embodiments described above may be made without departing from the spirit of the invention. The scope of the invention is solely defined by the appended claims.

We claim:

1. A method of determining the thickness of a retina, the method comprising:
    illuminating the retina with a beam of light;
    receiving, at a spectrometer, a reflected beam of light from the retina; and
    using an autocorrelation signal within the reflected beam of light to determine the thickness of the retina, wherein the autocorrelation signal is produced by different reflections of the beam of light, reflecting off different layers of the retina, interfering with each other, and wherein the autocorrelation signal is visible as more than noise.

2. The method of claim 1 wherein using the autocorrelation signal to determine the thickness of the retina comprises:
    applying a Fast Fourier Transform (FFT) to an optical frequency spectrum of the reflected beam of light to produce the autocorrelation signal; and
    determining the thickness of the retina from a strongest signal within the autocorrelation signal.

3. The method of claim 2 wherein determining the thickness of the retina comprises:
    determining the distance between a nerve fiber layer (NFL) and layers between an inner segment/outer segment (IS/OS) and a retinal pigment epithelium (RPE) from the strongest signal within the frequency spectrum; and
    deducing the thickness of the retina from the determined distance between the NFL and the layers between the IS/OS and the RPE.

* * * * *